(12) United States Patent
Masters

(10) Patent No.: US 9,517,158 B2
(45) Date of Patent: Dec. 13, 2016

(54) ADAPTIVE FLOATING FLANGE FOR OSTOMY APPLIANCE

(75) Inventor: Brock Edward Masters, Toronto (CA)

(73) Assignee: HOLLISTER INCORPORATED, Libertyville, IL (US)

( * ) Notice: Subject to any disclaimer, the term of this patent is extended or adjusted under 35 U.S.C. 154(b) by 906 days.

(21) Appl. No.: 13/223,504

(22) Filed: Sep. 1, 2011

(65) Prior Publication Data

US 2012/0059341 A1    Mar. 8, 2012

Related U.S. Application Data

(60) Provisional application No. 61/380,969, filed on Sep. 8, 2010.

(51) Int. Cl.
*A61F 5/448* (2006.01)

(52) U.S. Cl.
CPC .................................... *A61F 5/448* (2013.01)

(58) Field of Classification Search
USPC ................................................ 604/332–345
See application file for complete search history.

(56) References Cited

U.S. PATENT DOCUMENTS

| 3,523,534 | A |   | 8/1970  | Nolan    |         |
|-----------|---|---|---------|----------|---------|
| 4,419,100 | A |   | 12/1983 | Alexander|         |
| 4,681,574 | A |   | 7/1987  | Eastman  |         |
| 4,826,496 | A | * | 5/1989  | Ferguson | 604/339 |
| 4,834,731 | A |   | 5/1989  | Nowak et al. |     |
| 4,917,690 | A |   | 4/1990  | Hunger   |         |
| 4,973,323 | A |   | 11/1990 | Kaczmarek et al. | |
| 5,041,102 | A |   | 8/1991  | Steer et al. |     |
| 5,912,059 | A |   | 6/1999  | Jones et al. |     |
| 5,951,533 | A |   | 9/1999  | Freeman  |         |
| 6,905,483 | B2| * | 6/2005  | Newby et al. | 604/164.08 |
| 2007/0144996 | A1 | * | 6/2007 | Sawyer | 215/235 |
| 2008/0269698 | A1 | * | 10/2008 | Alexander et al. | 604/332 |

FOREIGN PATENT DOCUMENTS

| EP | 0519586    | 12/1992 |
| GB | 1568860    | 6/1980  |
| GB | 2225956    | 6/1990  |
| WO | 2009-023871| 2/2009  |

OTHER PUBLICATIONS

International Search Report for PCT/2011/050293, dated Sep. 14, 2012.
Image of Microduotec mushroom fastening system from Gottlieb Binder GmbH & Co., of Holzgerlingen, Germany, found at www.binder.de.
Written Opinion of the nternationai Search Authority in connection with PCT/2011/050293 flied Sep. , 2011.

* cited by examiner

*Primary Examiner* — Loan H Thanh
*Assistant Examiner* — Jennifer M Deichl
(74) *Attorney, Agent, or Firm* — Levenfeld Pearlstein, LLC

(57) ABSTRACT

An adaptive ostomy appliance includes a collection pouch, a first coupling ring attached to the collection pouch, and a faceplate having a second coupling ring assembly connected to it by a thermoplastic web. The coupling rings couple the faceplate to the pouch. A securing member releaseably, operably couples the second coupling ring with the front surface of the faceplate.

16 Claims, 2 Drawing Sheets

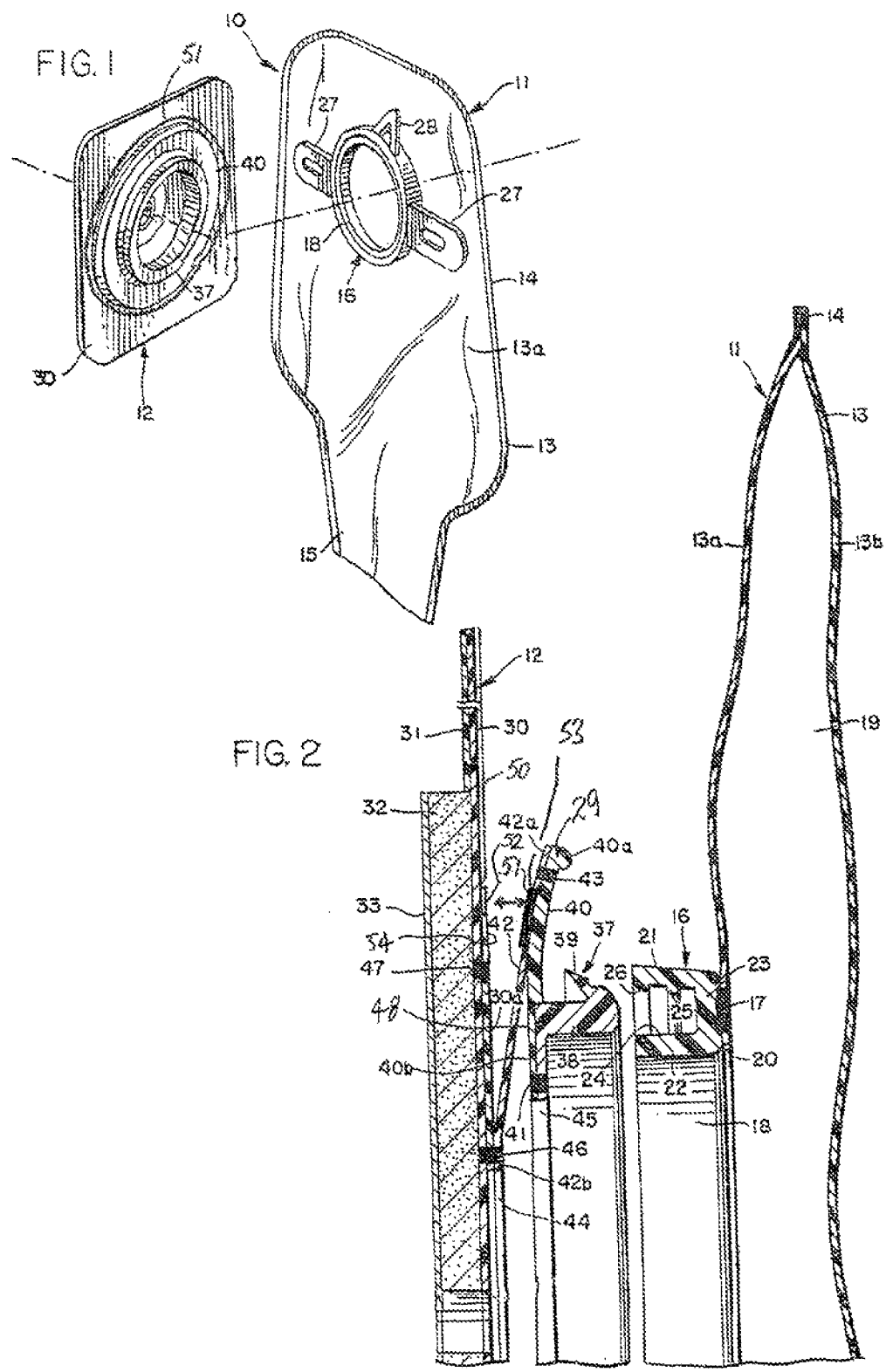

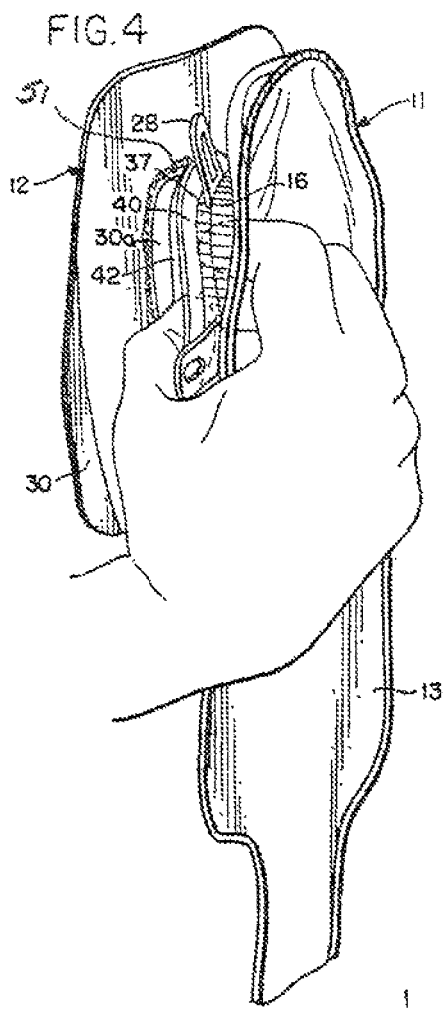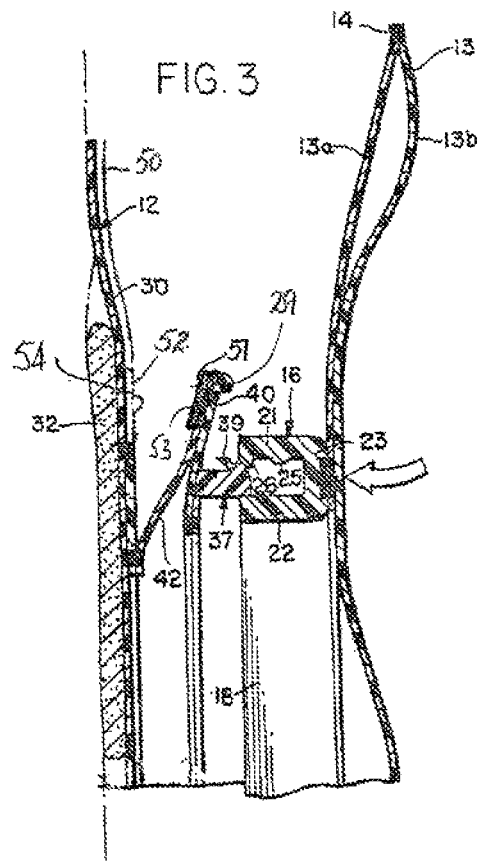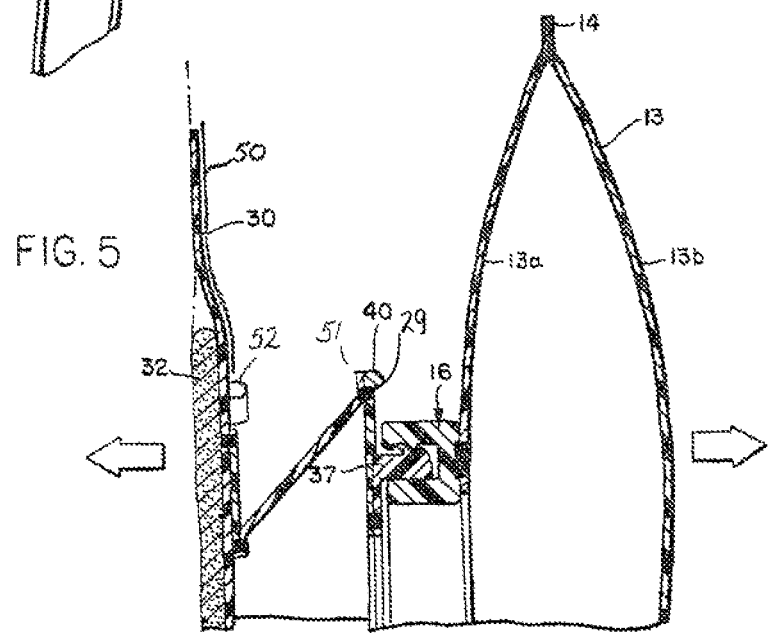

ADAPTIVE FLOATING FLANGE FOR OSTOMY APPLIANCE

CROSS-REFERENCE TO RELATED APPLICATION DATA

This application claims the benefit of priority of Provisional U.S. Patent Application Ser. No. 61/380,969, filed Sep. 8, 2010 entitled, "ADAPTIVE FLOATING FLANGE FOR OSTOMY APPLIANCE."

BACKGROUND

The present disclosure is directed to an ostomy device. More particularly, the present disclosure pertains to an adaptive flange for an ostomy appliance that is movable between a fixed position and a floating position.

An ostomy appliance or system is a medical device or prosthetic that provides a means for the collection of waste from a stoma, typically created as a result of a surgical procedure to divert a portion of the colon or small intestine. One type of ostomy appliance device is a pouch that is attached to the user's peristomal area, around the formed stoma.

There are two principal types of pouching systems, one-piece systems and two-piece system. In a one-piece system, a faceplate assembly which includes barrier element is adhered to the user's skin, surrounding the stoma. The barrier is a hydroscopic seal element that provides a waste/liquid/gas seal between the user's skin and the pouch. The pouch is directly adhered to an opposite side of the faceplate assembly or barrier. One-piece designs require that the user remove the entire appliance, including the faceplate or barrier, from the peristomal area to empty or flush the pouch or to replace the pouch.

Two-piece systems likewise include a barrier or a faceplate to adhere to the user's peristomal area. However, unlike one-piece systems, two-piece systems include one of a pair of coupling rings or flanges fixedly attached to the opposite side of the barrier. The collection pouch includes a coupling ring to mate with the barrier ring. The coupled rings or flanges attached mechanically to provide a seal. The two-piece design allows the user to remove the pouch, without removing the barrier that is adhered to the skin, to permit emptying, cleaning, venting or the like. The pouch can then be reapplied or a new pouch applied to the existing barrier or faceplate. The can help to reduce the discomfort and irritation associated with removing adhesive or gel from the skin.

One of the difficulties in use of the two-piece design is that is may be difficult to separate and join the pouch and barrier rings to one another. Since the barrier ring is so close to the user's body (peristomal area), it is necessary to urge one's fingers between the ring and the faceplate or barrier to grasp the barrier ring so that the pouch (and pouch ring) can be pulled to effect separation. This can be difficult for even those users with full dexterity and becomes more difficult for those that have less than full dexterity of those that are overweight.

To address this concern, two-piece designs have been developed that include a floating flange. In such an arrangement, the barrier ring or flange is mounted to the faceplate or barrier by a flexible membrane, such as a short, polymeric element that is scaled to both the faceplate or barrier and to the ring. The membrane serves as an extension piece between the faceplate/barrier and the barrier ring. This allows the barrier ring to be accessed slightly farther away from the barrier and the user's skin. It has been found that this configuration greatly increases the ability of those with both full dexterity, as well as those with limited dexterity or access to the peristomal area to grasp the barrier ring when removing the pouch.

While the two piece design functions well for its intended purpose, there are some drawbacks. For example, the increased distance between the user and the pouch (or the barrier and the pouch) and the flexible membrane can induce less of a secure feeling to the user. Also, with a floating flange, the pouch can tend to pull away from the user and therefore be more likely to be visible (e.g., create a noticeable bulge beneath the user's clothing), especially when the pouch contains a significant amount of stomal output. This can result in the user becoming less likely to maintain normal or active everyday activities.

Accordingly, there is a need for a flange that combines the low profile, security and other advantages of the fixed flange arrangement with the comfort, flexibility, and ease of use of the floating flange arrangement.

BRIEF SUMMARY

An adaptive ostomy appliance includes a collection pouch, a first coupling ring, a second coupling ring, a thermoplastic web, a faceplate, and a floating-flange securing medium. The first coupling ring is secured to the collection pouch and has a first opening therethrough in communication with the interior of the collection pouch. The flexible faceplate is adapted on a rear surface to be adhesively secured to the peristomal surface of a wearer's body. The second coupling ring assembly, having a floating flange, is mounted to a front surface of the faceplate by a thermoplastic web and is configured to couple with the first coupling ring of the collection pouch, to couple the faceplate with the collection pouch. The thermoplastic web resiliently and flexibly secures the second coupling ring assembly to the front surface of the faceplate. The floating flange securing mechanism is mounted or affixed to the rear surface of the flange or the front surface of the faceplate or both and may be an adhesive or mechanical device configured to secure the rear of the flange to the front surface of the faceplate to flush-mount the collection pouch.

The thermoplastic web is annular in configuration, having an outer edge portion secured to the periphery of the second ring and an inner edge portion secured to the faceplate about the aperture thereof. Together, the first and second coupling rings are detachably connectable to each other and configured to couple the pouch and the faceplate together, while the flange securing medium is configured to couple the rear surface of the floating flange of the second coupling ring assembly directly with the front surface of the faceplate.

In an embodiment, the flange may be positioned in a floating position or in a flush position. Additionally, the flange may be provided with a slight but definite curvature (when viewed in radial section) with the convex surface of the flange facing towards the faceplate, such that in a floating position, the flange is normally spaced a slight distance from the faceplate. The user has the option of securing the rear of the flange to the faceplate directly into the flush position, such that the flange no longer floats, but is relatively flat against the faceplate to present a sleeker, more discrete profile. In a flush position, the flange is positioned flat against the faceplate with a slight curvature or tab at the top of the flange.

A user may easily grasp the tab and disengage the faceplate from the rear of the flange without disrupting the first and second coupling rings. Furthermore, in the floating position, a user may easily and quickly insert his/her fingers between the flange and faceplate to brace the flange and the second coupling ring when the two coupling rings are to be latched together. Similarly, when the rings are to be disconnected, the second ring may be easily gripped by its enlarged flange portion and held in place while a tab is pulled away.

These and other features and advantages of the present disclosure will be apparent from the following detailed description, in conjunction with the appended claims.

BRIEF DESCRIPTION OF THE SEVERAL VIEWS OF THE DRAWINGS

The benefits and advantages of the present disclosure will become more readily apparent to those of ordinary skill in the relevant art after reviewing the following detailed description and accompanying drawings, wherein:

FIG. 1 is a perspective view of the ostomy appliance;

FIG. 2 is a sectional view of the ostomy appliance;

FIG. 3 is a sectional view of the ostomy appliance during a coupling operation;

FIG. 4 is a perspective view showing the parts as they might be oriented and held during a coupling operation; and FIG. 5 is a partial sectional view showing the coupling rings fully engaged and illustrating the optional securing of the floating flange to the faceplate of the ostomy appliance.

DETAILED DESCRIPTION

While the present disclosure is susceptible of embodiment in various forms, there is shown in the drawings and will hereinafter be described a presently preferred embodiment with the understanding that the present disclosure is to be considered an exemplification of the disclosure and is not intended to limit the disclosure to the specific embodiment illustrated.

It should be further understood that the title of this section of this specification, namely, "Detailed Description", relates to a requirement of the United States Patent Office, and does not imply, nor should be inferred to limit the subject matter disclosed herein.

FIG. 1 illustrates a two-part ostomy appliance 10 having a pouch assembly 11 and a faceplate assembly 12. The pouch assembly includes a collection pouch 13 which may be formed of two panels 13a and 13b joined together by a peripheral zone of heat sealing 14 and terminating in an open neck portion 15 at the pouch's lower end. Where such a neck portion is provided, a suitable clamp, such as the clamp disclosed in U.S. Pat. No. 3,523,534, or other means, can be used to maintain the pouch's lower end in a closed condition. Alternatively, neck portion 15 may be omitted entirely and the heat-scaling zone 14 may extend about the full periphery of the pouch.

A first coupling ring 16 is secured to one wall 13a of the pouch by heat sealing at 17 or by any other suitable means. The coupling ring 16 has a generally circular configuration, defining a central opening 18 which communicates with the rear 19 of the pouch through aperture 20 in the upper portion of panel 13a. When viewed in section, the coupling ring 16 is U-shaped, having spaced outer and inner walls 21 and 22 joined by an integral intermediate wall 23, the latter being secured by heat seal 17 to panel 13a of the pouch. The channel 24 of the coupling ring 16 therefore faces away from pouch 13 in a generally rearward direction with respect to the wearer. Within channel 24, a pair of latching ribs 25 and 26 are provided by outer wall 21. Referring to FIG. 1 a pair of apertured tongues 27 may project laterally from opposite sides of the coupling ring 16 for the attachment of a suitable support belt, if the use of such a belt is desired by the wearer. An integral tab 28 also projects radially outwardly from the periphery of coupling ring 16 to serve as a handle for pulling ring 16 away from the faceplate assembly 12 during an uncoupling operation.

In the embodiment illustrated, the faceplate assembly 12 includes a highly flexible faceplate 30 preferably formed of a gas-penetrable, water-resistant microporous material. The faceplate is preferably highly flexible, so that it will conform readily to body contours and body movements, and relatively strong and durable. It can be coated on its back or rear side with a medical-grade pressure-sensitive adhesive so that upon removal of backing sheets 31 the microporous faceplate may be adhesively secured to the patient's skin in the peristomal region.

The backside of the faceplate 30 may be formed as or have a resilient sealing ring or barrier 32 secured thereto. The barrier can be formed of a variety of pliable and tacky material capable of sealingly engaging the peristomal area to prevent the escape of liquids and gases. Such barrier materials are well know in the art. Where provided, such a ring and/or the entire rear side of the faceplate would have its rear surface covered by a removable release or backing sheet 33 as shown in FIG. 2.

A second coupling ring 37 is mounted upon faceplate 30 in the manner shown most clearly in FIGS. 2-4. In the particular embodiment illustrated, the second coupling ring includes an insert portion 38 adapted to be received within the channel 24 of the first coupling ring 16. The insert portion has an integral spring latching member 39 which is engageable with outer wall 21 of ring 16 to perform the dual functions of forming a fluid-tight seal between the parts and of establishing a double-latch that locks the two rings against unintentional disconnection (FIG. 5). The second coupling ring 37 also includes a radially- and circumferentially-extending annular flange portion 40. In the illustration given, flange portion 40 and insert portion 38 are formed separately and are heat sealed together at 41; however, the two portions might be integrally formed if such a construction were desired. It will be observed that flange portion 40 extends a substantial distance radially outwardly beyond the two coupling rings 16, 37, and is provided with a bead 40a about the outer perimeter thereof. In a relaxed or untensioned state, the annular flange portion 40 has a gentle forward curvature (when viewed in radial section as in FIG. 2) so that its rear surface 40b—the surface facing faceplate 30—has a slight convex curvature.

The particular coupling ring assembly depicted in the drawings utilizes a double-ribbed channel construction and a spring member 39 that cooperates with both ribs within the channel to produce a highly effective sealing interlock between the parts. It is to be understood that the floating feature disclosed in the present application may be used with other types of coupling rings. Such a coupling ring is more fully discussed in Alexander, U.S. Pat. No. 4,419,100, which is commonly assigned with the present application and is incorporated herein by reference.

A thin annular web 42 of flexible and resilient thermoplastic material joins the periphery of flange portion 40 to faceplate 30. The outer edge portion 42a of the thermoplastic web 32 can be heat scaled at 43 to the periphery of flange portion 40, and the inner edge portion 42b, which defines an opening 44 of smaller diameter than opening 45 of ring 37, is joined by heat seal 46 to the faceplate 30. In the embodiment illustrated, the faceplate 30 includes an annular mounting collar 30a which reinforces the faceplate 30 in the area about opening 44 and heat seal 46. The collar 30a is secured to the remainder of the faceplate 30 by a second heat seal 47, as illustrated in FIG. 2. This configuration, which provides a floating flange, is described in the aforementioned patent to Alexander.

In an effort to provide a more secure arrangement between the pouch 13 and the faceplate 30 when the rings 16, 37 are secured to one another, the present adaptive floating flange 40 permits releaseably securing the pouch 13 to the faceplate 30. In one configuration, the rear surface 48 of the faceplate flange 40b has a flange securing member 51. The flange securing member 51 can be an adhesive or a mechanical device such as a snap, latch, mushroom-type, or hook and loop type securing mechanism, as illustrated. Depending on the securing member used, a corresponding securing member 52 may be positioned on the faceplate 30 in opposing relation to the flange securing member 51. For example, if a mushroom-type system or a hook and loop type fastener is used, one portion, such as one mushroom member, or the hook portion 53, can be affixed to the faceplate flange 40b, while the other portion, the other mushroom member or the loop portion 54 can be affixed to the faceplate 30. After the pouch 13 and faceplate flanges 40b are secured to one another, the members (for example, the mushroom-type or hook and loop 53, 54 elements) can be secured to each other. This reduces the distance between the pouch 13 and the user's skin, and provides a more secure feeling that the pouch 13 is secured to the user. The securing members 51, 52 enable the rear of the flange 40b to be secured to the faceplate 30 by releaseably joining the securing members 51, 52 to one another. The thin annular web 42 is compressed between the faceplate 30 and the flange 40 when the flange securing member 51, 52 are engaged. One exemplary type of a mushroom-type fastening system is that available under the trademark MICRODUOTEC, available from Gottlieb Binder GmBH & Co., of Holzgerlingen, Germany.

The advantages of the adaptive floating relationship between coupling ring 37 and faceplate 30 is indicated in FIGS. 3-5. The annular web 42 allows a wearer (or a nurse or other attendant to place his/her fingers behind the second coupling ring 37, that is, between the coupling ring and faceplate 30, to better grasp the ring 37 so that it may be coupled to ring 16. The coupling action is carried out simply by squeezing the two rings 16, 37 together in the manner illustrated in FIG. 4. In that view, the wearer's thumb is inserted behind web 42 and coupling ring 37, and other fingers engage wall 13b of the pouch which in turn contacts wall 13a to force the rings 16, 37 together into the fully coupled positions depicted in FIG. 5. The interlocking of the two coupling rings 16, 37 is therefore achieved without urging ring 37 rearwardly and without exerting pressure on the tender peristomal area. Since the limited floating relationship between ring 37 and faceplate 30 allows the user's fingers to directly contact the rear surface of web 42 in bracing the coupling ring 37 during a coupling operation, such contact promotes tactile confirmation that a coupling or latching action has in fact occurred. Such tactile confirmation is particularly effective if the coupling rings are constructed to produce a snap action as they are latched together.

Once the rings 16, 37 are coupled, however, the user has the option of leaving the flange 40 free from the faceplate, that is to "float", or to secure the rear surface 40b of the flange 40 to the faceplate 30 to achieve a more flush profile and a more secure feeling that the pouch 13 is held in place, using the flange securing members 51, 52. In a preferred embodiment, the user need only press the flange gently toward the faceplate 30 to engage the flange securing members 51, 52 to each other. Alternately, the user may use tactile sensation to locate corresponding portions of a mechanical type securing member 51, 52, such as a snap or hook-and-latch mechanism, and couple the corresponding portions together.

It will be appreciated that one or more types of securing members 51, 52 can be used and that all or some of the securing members 51, 52 may be engaged or coupled when securing the flange 40 to the faceplate 30. It is also contemplated that multiple sets of members 51, 52 (in the case of mechanical securing members) can be present at desired locations around the flange 40 and on the faceplate 30. For example, a set of members can be present at a 12 o'clock position, and at a 6 o'clock position to provides upper and lower fastening locations. Alternately, if a temporary or removable adhesive is used, the adhesive can be applied fully around (i.e., 360 degrees) the flange or, again, only at desired locations as appropriate. Those skilled in the art will appreciate the various types of securing members or securing media that can be used and the locations of the members or media, all of which are within the scope and spirit of the present disclosure.

Uncoupling of the flange 40 from the faceplate 30 is achieved by gently pulling on the flange or, if present, tab 29 in a forward direction, away from the faceplate 30. The flange securing members 51, 52 will then uncouple, leaving the flange 40 in a floating position, with the rings 16, 37 coupled.

Uncoupling of the rings is achieved by gripping tab 28 and pulling it radially outwardly (to disengage a portion of rib 26 from latching member 39) and then forwardly. During such operation, the wearer (or other person) immobilizes ring 37 by gripping flange 40 in the area adjacent tab 28. Again, such action may be carried out without transmitting any appreciable forces to the faceplate that might cause patient discomfort or result in separation (or weakening) of the adhesive seal between the faceplate and the patient.

The advantages to the present adaptive floating flange will be appreciated by those skilled in the art. The present flange arrangement eliminates pressure on tender peristomal areas abdomens with the floating flange arrangement and protects the skin over extended wearing time. It also gives the user more flexibility regarding changes in the profile of the ostomy appliance depending on needs, without compromising its integrity. The present flange arrangement provides a non-rigid, extended interconnection between the deformable faceplate and the coupling ring assembly, allowing the ring assembly to float to a limited extent with respect to the faceplate, while providing a way in which the flanges (and pouch) can be temporarily secured to the faceplate and user to present a more flush profile, and a greater sense of security that the pouch is properly and appropriately secured in place.

All patents referred to herein, are incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. An ostomy appliance comprising: a collection pouch;
a first coupling ring attached to the collection pouch, the first coupling ring having a first opening therethrough in communication with the pouch;
a faceplate having a rear surface and a front surface;
a second coupling ring adapted to sealingly mate with the first coupling ring;
a web operably connecting the second coupling ring to the faceplate, the second coupling ring having a second opening corresponding to the first opening and a flange encircling the second opening, wherein the second coupling ring and the first coupling ring are configured to couple the pouch and the faceplate together; and
a securing member configured to releaseably, operably couple the second coupling ring with the faceplate.

2. The ostomy appliance in accordance with claim 1 wherein the securing member is an adhesive.

3. The ostomy appliance in accordance with claim 1 wherein the securing member is a multi-pan mechanical fastening element.

4. The ostomy appliance in accordance with claim 3 wherein the multi-part mechanical fastening element is a snap, a hook and latch device or a hook and loop fastener.

5. The ostomy appliance in accordance with claim 4 including multiple multi-part mechanical fastening elements.

6. The ostomy appliance in accordance with claim 1 wherein the securing member is present on a rear surface of the second coupling ring.

7. The ostomy appliance in accordance with claim 1 wherein the securing member is present on the front surface of the faceplate.

8. The ostomy appliance in accordance with claim 1 wherein a portion of the securing member is present on a rear surface of the second coupling ring and another portion of the securing member is present on the front surface of the faceplate.

9. A faceplate for use with a two-piece ostomy appliance, the two-piece ostomy appliance including a pouch having a first coupling ring, the faceplate comprising:
a second coupling ring adapted to sealingly mate with the first coupling ring;
a web operably connecting the second coupling ring to the faceplate, the second coupling ring having an opening therein, and a flange encircling the opening, wherein the second coupling ring and the first coupling ring are configured to couple the pouch and the faceplate together; and
a securing member configured to releaseably, operably couple the second coupling ring with the faceplate.

10. The faceplate in accordance with claim 9 wherein the securing member is an adhesive.

11. The ostomy appliance in accordance with claim 9 wherein the securing member is a multi-part mechanical fastening element.

12. The ostomy appliance in accordance with claim 11 wherein the multi-part mechanical fastening element is a snap, a hook and latch device or a hook and loop fastener.

13. The ostomy appliance in accordance with claim 12 including multiple multi-part mechanical fastening elements.

14. The ostomy appliance in accordance with claim 9 wherein the securing member is present on a rear surface of the second coupling ring.

15. The ostomy appliance in accordance with claim 9 wherein the securing member is present on the front surface of the faceplate.

16. The ostomy appliance in accordance with claim 9 wherein a portion of the securing member is present on a rear surface of the second coupling ring and another portion of the securing member is present on the front surface of the faceplate.

* * * * *

UNITED STATES PATENT AND TRADEMARK OFFICE
CERTIFICATE OF CORRECTION

PATENT NO.         : 9,517,158 B2                               Page 1 of 1
APPLICATION NO.    : 13/223504
DATED              : December 13, 2016
INVENTOR(S)        : Masters It is certified that error appears in the above-identified patent and that said Letters Patent is hereby corrected as shown below:

On the Title Page

Item [56], Column 2, Line 6, delete "nternationai" and insert --International--.

In the Specification

Column 3, Line 53 approx., delete "heat-scaling" and insert --heat-sealing--.

Column 4, Line 63 approx., delete "scaled" and insert --sealed--.

In the Claims

Column 7, Line 23, Claim 3, delete "multi-pan" and insert --multi-part--.

Signed and Sealed this
Twenty-first Day of March, 2017

Michelle K. Lee
*Director of the United States Patent and Trademark Office*